US011970675B2

(12) United States Patent
Kong

(10) Patent No.: US 11,970,675 B2
(45) Date of Patent: *Apr. 30, 2024

(54) DEVICES, SYSTEMS AND METHODS OF MAKING AND USING CHLORINE DIOXIDE BASED FORMULATION WITH IMPROVED STABILITY

(71) Applicant: Spectrum Doxyicide LLC, Denver, CO (US)

(72) Inventor: Stephen Bradford Kong, Alamo, CA (US)

(73) Assignee: SPECTRUM DOXYICIDE, Denver, CO (US)

( * ) Notice: Subject to any disclaimer, the term of this patent is extended or adjusted under 35 U.S.C. 154(b) by 632 days.

This patent is subject to a terminal disclaimer.

(21) Appl. No.: 17/143,141

(22) Filed: Jan. 6, 2021

(65) Prior Publication Data
US 2021/0122999 A1 Apr. 29, 2021

Related U.S. Application Data

(63) Continuation-in-part of application No. 16/995,804, filed on Aug. 17, 2020, now Pat. No. 11,497,215, which is a continuation-in-part of application No. 16/884,033, filed on May 26, 2020, now Pat. No. 11,523,608, which is a continuation-in-part of application No. 15/997,660, filed on Jun. 4, 2018, now Pat. No. 10,660,339.

(51) Int. Cl.
*C11D 3/48* (2006.01)
*C11D 3/00* (2006.01)
*C11D 3/04* (2006.01)

(52) U.S. Cl.
CPC .............. *C11D 3/48* (2013.01); *C11D 3/0047* (2013.01); *C11D 3/042* (2013.01); *C11D 3/044* (2013.01)

(58) Field of Classification Search
CPC ......... C11D 3/48; C11D 3/0047; C11D 3/042; C11D 3/044
See application file for complete search history.

(56) References Cited

U.S. PATENT DOCUMENTS

| | | | | |
|---|---|---|---|---|
| 5,932,085 A | * | 8/1999 | Cowley | C02F 1/4674 |
| | | | | 423/478 |
| 9,788,549 B2 | * | 10/2017 | Wood | A01N 59/00 |
| 10,660,339 B2 | * | 5/2020 | Kong | A01N 59/00 |
| 11,497,215 B2 | * | 11/2022 | Kong | A61L 2/18 |
| 11,523,608 B2 | * | 12/2022 | Kong | C01B 11/024 |
| 2003/0004216 A1 | * | 1/2003 | Birnbaum | A61K 31/14 |
| | | | | 514/643 |
| 2011/0256244 A1 | * | 10/2011 | Abe | A01N 59/00 |
| | | | | 424/661 |
| 2015/0237864 A1 | * | 8/2015 | Wood | A01N 59/00 |
| | | | | 424/661 |

* cited by examiner

*Primary Examiner* — Blessing M Fubara
(74) *Attorney, Agent, or Firm* — Michael R Shevlin

(57) ABSTRACT

Disclosed are devices, systems, and methods for producing broad spectrum disinfectants, sanitizers, cleaner and deodorizers using chlorine dioxide compositions, and more particularly, to methods for producing chlorine dioxide compositions having improved long term stability by the proper choice of pH and through the careful choice of other product formula ingredients.

19 Claims, 6 Drawing Sheets

DEVICES, SYSTEMS AND METHODS OF MAKING AND USING CHLORINE DIOXIDE BASED FORMULATION WITH IMPROVED STABILITY

CROSS-REFERENCE TO RELATED APPLICATIONS

This application is a continuation-in-part to U.S. patent application Ser. No. 16/995,804, filed Aug. 17, 2020, which is a continuation-in-part to U.S. patent application Ser. No. 16/884,033, filed on May 26, 2020, which is a continuation-in-part to U.S. patent application Ser. No. 15/997,660, filed on Jun. 4, 2018, which is related to commonly owned U.S. application Ser. No. 14/631,806 titled BROAD SPECTRUM DISINFECTANT, filed on Feb. 25, 2015, which claims priority to U.S. Provisional Application No. 61/945,054, filed Feb. 26, 2014, which are incorporated herein by reference.

FIELD

The present invention is generally related to broad spectrum disinfectants, sanitizers, antiseptics, fungicides, cleaners or deodorizers using chlorine dioxide compositions, and more particularly, to methods for producing chlorine dioxide compositions having improved long term stability by the proper choice of pH and through the careful choice of other product formula ingredients.

BACKGROUND

For a product to be successful in the marketplace, it must have suitable shelf life stability, in addition to, providing the desired function and aesthetics. Disinfecting or sanitizing products require a suitable biocidal agent. Some examples of biocides are chlorine dioxide, hypochlorite, peroxide, and quaternary amines. Many products containing reactive ingredients such a chlorine dioxide (ClO2) have problems with long-term stability, thus limiting their shelf-life. Chlorine dioxide is an effective biocide and can clean and deodorize. One particular advantage of ClO2 over hypochlorite is that ClO2 does not chlorinate organic compounds. However, it is inherently less stable than other biocides such as quaternary amines. Due to instability, most applications involve producing chlorine dioxide at the source of use. Therefore, chlorine dioxide must be properly formulated to be viable.

Products containing chlorine dioxide generally have a limited shelf life because chlorine dioxide decomposes over time even in closed bottles. Typically, unstable products will have a use by or expiration date to ensure that the product's designated performance, such as micro efficacy, is maintained throughout the time period. Manufacturing and inventory control, as well as, maintaining microbiological efficacy are therefore challenging for product with limited lifetime. Due to its inherent instability, chlorine dioxide is often produced at the source using a chlorine dioxide generator. Another approach is to market a 2-Part (or multipart) product where the precursors of the active ingredients are mixed/reacted at the point of use, and then specify an appropriate time period to use the product. However, 2-Part products generally require more complex packaging, and require the consumer to perform an extra "mixing" step before using. There is also a risk that that the mixing/reacting step is not followed properly. This extra mixing step may not be desirable to the consumer and the consumer may prefer an alternative product. Yet another approach could be using a package and a trigger/pump dispenser system that keeps the reagents separated until use. In this scenario, a multiple (dual) chamber bottle equipped with a trigger/pump actuator having a dip (supply) tube inserted in each chamber such that when the trigger/pump actuator is used, aliquots from both chambers are simultaneously drawn and mixed when dispersed. This approach would require a more complex bottle and trigger/actuator due to the multiple product streams. Additionally, more time is needed for a chemical reaction to occur with a more complex package so the biocidal effect is slower.

In view of this, it is desirable to develop a disinfectant or sanitizing or cleaner/deodorizer product that maximizes the stability of the active ingredients so that the product has a suitable shelf-life and is ready to use after manufacturing. Stable products have a longer shelf-life, better consumer appeal, and are easier to use. A stable product can use conventional packaging that is readily available and cheaper.

SUMMARY

In one aspect, the invention is a device for delivering stabilized chlorine dioxide having improved long term stability by the proper choice of pH. A number of synthesis reactions are known for producing chlorine dioxide. The preferred method is the acidification of chlorite.

ClO2 may be produced in a batch process or a continuous process using Hydrochloric acid solution (HCl), Sodium chlorite ($NaClO_2$), Sodium Hydroxide (NaOH) and Deionized water ($H_2O$).

Any suitable acid may be used in the process disclosed. By suitable, we define a suitable acid to be one that reacts with NaClO2 to produce ClO2, and is compatible with ClO2. Acids may be moderate to strong acids that are capable of reacting with sodium chlorite to form ClO2.

The reaction of NaClO2 with an acid is used to produce ClO2. The process may be done using a combination (mixture) of acids rather than just using one acid.

A concentrated product could have applications such as a floor cleaner, general cleaner/deodorizer, use in toilet bowl, or in laundry applications. The concentrated product is a product that may be used full strength or be diluted prior to use.

In some embodiments surfactant and/or other adjuncts can be added to the basic solution to create a range of products. Surfactants help facilitate cleaning and wetting of surfaces to improve the micro efficacy of chlorine dioxide.

Gum thickeners can be added to thicken the product to improve contact time on a vertical surface or potentially as in a hand sanitizer.

Product Applications/Uses

ClO2 products include sanitizer or disinfectant, floor cleaner, general cleaner/deodorizer, use in toilets, or in laundry applications. The product may be used along or combined with other products. ClO2 can kill germs, clean, deodorize, and destroy allergens on hard or soft surfaces on hard and soft surfaces for household, commercial and healthcare (including equipment) with bacterial, viral and fungal diseases or contamination, decontamination into and out of health care units, etc.

Laundry

The product could be added to sanitize, clean, deodorize or remove stains or destroy allergens on soft surfaces. It could be added through the wash, or added in the rinse cycle (i.e., post cleaning). High efficiency wash machines generally have chambers for various cleaning ingredients. Regular wash machines often have dispensers mounted on the agitator that dispense by centrifugal force to add a fabric softener during the rinse cycle. A dispensing ball or other device in the washing machine that could release the ClO2 after the wash step are also possible. There could be injectors or other approaches to deliver the ClO2 to the wash or post-wash.

Decontamination of Clothing or Equipment

ClO2 could be used for decontamination of hazmat suits or equipment. It could be used on farming equipment etc. to prevent transfer of bacteria/pathogens from one crop field to another.

Hard Surfaces

Used full strength or diluted for use on toilet bowl, sinks, cutting boards, highchairs, baby/child toys, pacifiers, upholstery, kitchen utensils, floors, laundry, etc.

ClO2 may be used for allergen control or allergen destruction. Allergens are proteins that cause an allergic response in our bodies. Runny noses and watery eyes are typical responses to allergens. Reducing the level of the allergen is needed to alleviate the allergic response. ClO2 can clean, kill germs, deodorize and reduce allergens. Allergen destruction could be desirable in a carpet cleaner, floor cleaner, or fabric treatments such as in laundry or on furniture.

Fruit Veggie Wash

A concentrated product could be diluted and used as a wash for fruits and vegetables. Fruits and veggies could be washed just as they are harvested or could be washed in the consumer's home before eaten. Reducing molds could reduce spoilage and extend the storage of fruits and veggies.

Personal Care for Humans

The product may be used on "human surfaces" to control bacterial, viral and fungal diseases or contamination, e.g., mouthwash, a gargle, rinse or other for throat, nose, douches skin, wounds or other internal uses.

ClO2 in either a concentrate or ready to use product could be used in applications such as; mouth wash, body wipe (perhaps used in-between bathing), wound care, treatment for skin infections or acne, and a potential remedy for poison oak.

Decontamination

The product may be used for decontamination before transportation (use as foot wash for shoes boots equipment, tires, etc.) when travelling between countries or sensitive agricultural or wildlife areas; e.g., the spread of fungal contamination to the sensitive frog populations of the world by the boots and other equipment of biologists studying the various populations can be prevented with use of a ClO2 decontamination wash. Additionally, use of a wash or spray on plants contaminated by fungus or other pests can save crops or other plant life.

Animals

The product may be used with animals both domesticated and wild to prevent fungal, viral and bacterial diseases.

Swimming Pools

ClO2 could have applications in swimming pools and spas where ClO2 could be an alternative to sodium hypochlorite or sodium hypobromite.

Mold/Mildew

ClO2 kills mold and the mold can be decolorized by ClO2.

Teeth Whitening

As previously discussed, the product may be used as a mouth wash/oral rinse etc. In addition ClO2 products could possibly be used to whiten teeth.

The device includes a delivery device configured to deliver a solution to a target application and a stabilized chlorine dioxide (ClO2) product that is configured to be delivered using the delivery device. The chlorine dioxide is produced using a method that includes adding a first amount of Hydrochloric acid (HCl) to a second amount of Sodium chlorite (NaClO2) that is dissolved in water, the first amount being greater than the second amount; agitating the HCl and NaClO2 for at least 10-30 minutes to mix the chemicals and thus allowing the chemical to react to completion; adding a third amount of DOWFAX 3B2 (i.e., sodium alkyl diphenyloxide disulfonate) to the solution and slowly agitate the HCl, NaClO2 and DOWFAX 3B2 solution to distribute the DOWFAX 3B2; and after the reaction to generate chlorine dioxide (ClO2) in solution has gone to completion, adding a fourth amount of Sodium Hydroxide (NaOH) to adjust the pH of the resulting ClO2 solution to a desired pH and concentration. Additional water or surfactant can be added to adjust the concentration of ClO2 or surfactant. It is understood that other alkali metal salts of chlorite and hydroxide can also be used and/or that mixtures of these salts can be used.

In another aspect, the invention is a method of making a high concentration chlorine dioxide with improved long-term stability. The method includes adding 42.61 g/l 10% Hydrochloric acid (HCl) to 3.20 g/l Sodium chlorite (NaClO2) dissolved in water; agitating the HCl and NaClO2 for at least 10-30 minutes to mix the chemicals; adding 1.50 g/l of DOWFAX 3B2 (i.e., sodium alkyl diphenyloxide disulfonate) and slowly agitate the HCl, NaClO2 and DOWFAX solution to distribute the DOWFAX; and adding 42.23 g/l of 5% Sodium Hydroxide (NaOH) to adjust the pH of the ClO2 solution to a desired pH.

In another aspect, the invention is a method for producing a high concentration chlorine dioxide with improved long-term stability. The method includes 1) adding a molar excess concentration amount of Hydrochloric acid (HCl) to an amount of Sodium chlorite (NaClO2) dissolved in an amount of water; 2) agitating the HCl and NaClO2 until the reaction to form chlorine dioxide (ClO2) is complete; 3) adding an amount of DOWFAX (i.e., sodium alkyl diphenyloxide disulfonate) and slowly agitating the HCl, NaClO2 and DOWFAX solution to distribute the DOWFAX; and 5) adding an amount of Sodium Hydroxide (NaOH) to the ClO2 solution to adjust the pH to a target value; wherein: the molar excess concentration amount of acid=42.61 g/l 10% HCl; the amount of sodium chlorite=3.20 g/l NaClO2 (80%); the amount of DOWFAX=1.50 g/l DOWFAX; the amount of NaOH=42.23 g/l of 5% NaOH; the pH target value approximately 4.5-6.5.

In some embodiments, the delivery device is a spray bottle and the stabilized ClO2 is a sprayable solution; the delivery device is a wipe and the stabilized ClO2 is a solution integrated into the wipe; the delivery device is a tablet and the stabilized ClO2 is integrated into the tablet; the delivery device delivers a laundry detergent and the stabilized ClO2 is integrated into the laundry detergent; the delivery device delivers a deodorizer and the method of producing the ClO2 further comprises adding a fragrance ingredient compatible with ClO2; the delivery device is a cleaning device and the stabilized ClO2 is produced as a concentrate that can be used at full strength or diluted with water.

In some embodiments, the desired pH 4.5-6.5. In some embodiment the ClO2 concentration is 1200-1300 PPM. In some embodiment the ClO2 concentration is 1250 PPM In some embodiments, the ClO2 is a spray solution configured to work with a spray bottle; the ClO2 is a concentrated solution configured to be used at full strength or diluted with water prior to use; the method further comprising adding a fragrance ingredient compatible with ClO2 to produce a fragranced solution.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

DETAILED DESCRIPTION

Figure 1:
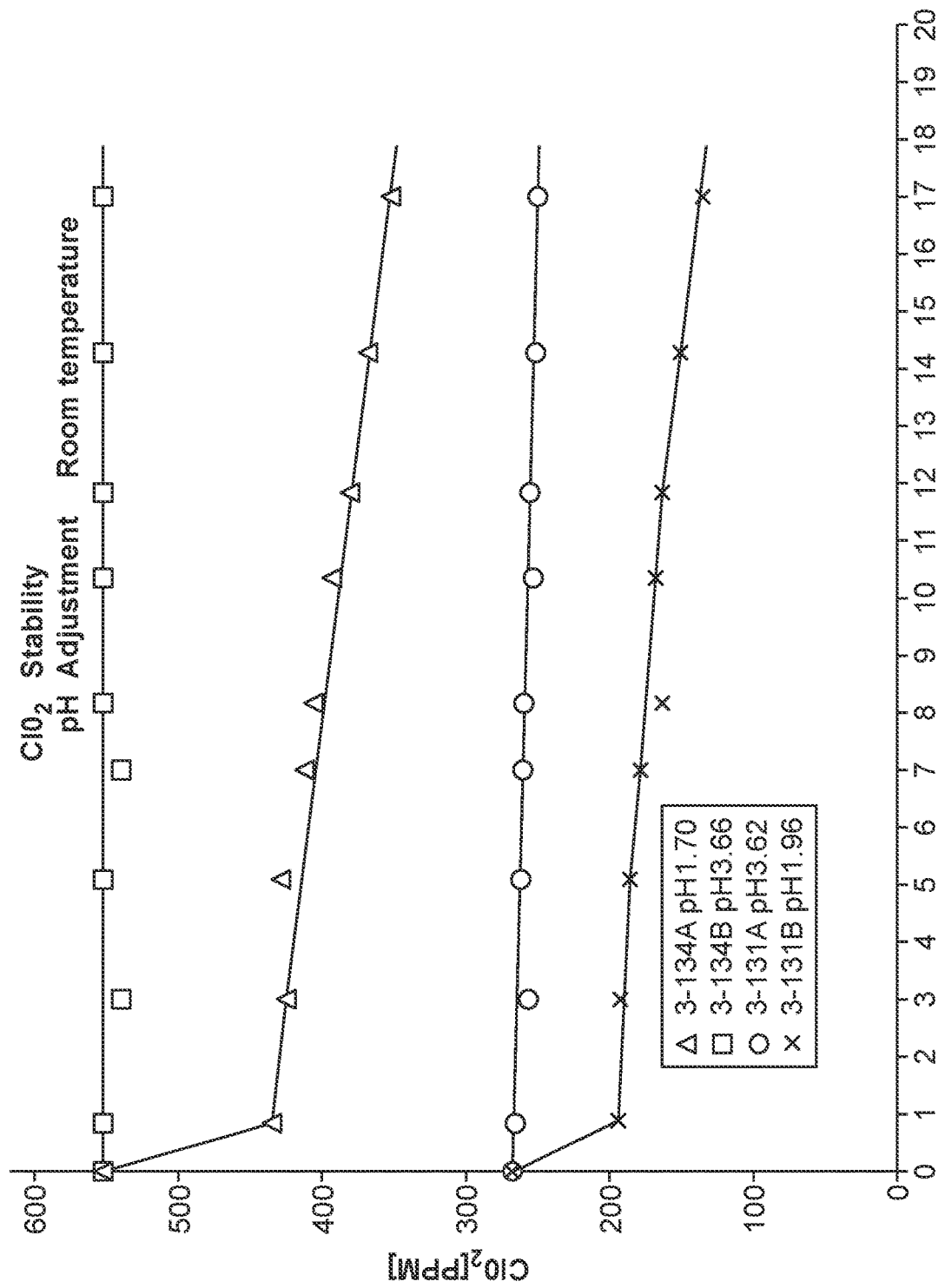
FIG. 1 shows a stability profile of chlorine dioxide compositions with differing pH levels vs. time.

Embodiments of the invention will now be described with reference to the figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

The present invention is directed to improve the stability of chlorine dioxide (ClO2) compositions and products. The inventor has found that the stability of the chlorine dioxide can be significantly improved by the proper choice of pH, and through the careful choice of other product formula ingredients. By maximizing the stability of chlorine dioxide, the product has a suitable shelf-life and is ready to use after manufacturing. This stabilization benefit applies regardless of the reaction method used to produce chlorine dioxide.

The improved stability of ClO2 is due to adjusting the pH. The relationship between pH and stability has not been e recognized, and that could explain the limited number of ClO2 based product in the market. The increased stability of ClO2 would make a product more desirable than a similar product with limited shelf-life, or a product that must be mixed prior to use.

Chlorine dioxide (ClO2) can be produced by a number of reactions with sodium chlorite (NaClO2). Several industrial methods of synthesis of chlorine dioxide are known such as acidification of chlorite, oxidation of chlorite by chlorine, oxidation of chlorite by persulfate. Other suitable reactions include the reaction of acetic anhydride with chlorite, the reduction of chlorates by acidification in the presence of oxalic acid, and the reduction of chlorates by sulfurous anhydride. Acidification of chlorite according to the following reaction is particularly appealing due to the availability, cost and ease of use of hydrochloric acid. It is understood that regardless of the method used to produce chlorine dioxide, the stability of the solution is controlled by pH and the proper choice of other ingredients.

Some examples of interest are discussed below. It is envisioned that the ClO2 product disclosed herein may be used in many applications and in different products depending on the final dilution and concentration. For example, in some embodiments the ClO2 product may be used in the laundry to sanitize, clean, deodorize or remove stains or destroy allergens on soft surfaces. In some embodiments the ClO2 product may be used to clean, sanitize and/or disinfect floor, carpet, rug, drapes, bedding and furniture. In some embodiments the ClO2 product may be used for stain removal and cleaning of floor, carpet, rug, furniture, drapes, bedding and other soft fabrics. In some embodiments the ClO2 product may be used for odor control of floor, carpet, rug, furniture and drapes. In some embodiments the ClO2 product may be used for disinfecting and sanitizing drapes, curtains, privacy screens, walls and floors and other materials and surfaces in hospitals. In some embodiments the ClO2 product may be used against pathogens, mold and fungi in healthcare/medical facilities. In some embodiments the ClO2 product may be used for cleaning, sanitizing and disinfecting soft toys, plastic toys, pacifiers, and other baby and childcare equipment, including but not limited to, high chairs, child car seats, push chairs and prams, swings, baby carriers, bikes, scooters, play pens. In some embodiments the ClO2 product may be dispensed in aerosol devices to restrain or disinfect airborne bacteria to improve the indoor air quality.

ClO2 may be used for allergen control or allergen destruction. Allergens are proteins that cause an allergic response in our bodies. Runny noses and watery eyes are typical responses to allergens. Reducing the level of the allergen is needed to alleviate the allergic response. ClO2 can clean, kill germs, deodorize and reduce allergens. Allergen destruction could be desirable in a carpet cleaner, floor cleaner, fabrics such as laundry or on furniture.

Other uses of the ClO2 product include sanitizer or disinfectant, floor cleaner, general cleaner/deodorizer, use in toilets, mouthwash or in laundry applications. The product may be used along or combined with other products.

In some embodiments the present invention is directed to improve the stability of chlorine dioxide (ClO2) compositions and products by the proper choice of pH, and through the careful choice of other product formula ingredients. By maximizing the stability of chlorine dioxide, the product has a suitable shelf-life and is ready to use after manufacturing.

In some embodiments the device includes a delivery device configured to deliver a solution to a target application and a stabilized chlorine dioxide (ClO2) product that is configured to be delivered using the delivery device. The chlorine dioxide is produced using a method that includes adding a first amount of Hydrochloric acid (HCl) to a second amount of Sodium chlorite (NaClO2) that is dissolved in water, the first amount being greater than the second amount; agitating the HCL and NaClO2 for at least 10-30 minutes to mix the chemicals and thus allowing the chemical to react to completion; adding a third amount of DOWFAX 3B2 (i.e., sodium alkyl diphenyloxide disulfonate) to the solution and slowly agitate the HCl, NaClO2 and DOWFAX solution to distribute the DOWFAX; and after the reaction to generate chlorine dioxide (ClO2) in solution has gone to completion, adding a fourth amount of Sodium Hydroxide (NaOH) to adjust the pH of the resulting ClO2 solution to a desired pH. Additional water or surfactant can be added to adjust the concentration of ClO2 or surfactant. Alternatively, sodium chlorite can be added to HCl such that the amount of HCl is greater than the amount of NaClO2, agitating the NaClO2 and HCl for at least 10-30 minutes allowing the chemicals to react to completion followed by adding DOWFAX 3B2 and adjusting pH by addition of NaOH.

In some embodiments the invention is a method of making a high concentration chlorine dioxide with improved long-term stability comprising. The method includes adding 42.61 g/l 10% Hydrochloric acid (HCl) to 3.20 g/l Sodium chlorite (NaClO2) dissolved in water; agitating the HCl and NaClO2 for at least 10-30 minutes to mix the chemicals; adding 1.50 g/l of DOWFAX 3B2 (i.e., sodium alkyl diphenyloxide disulfonate) and slowly agitate the HCl, NaClO2 and DOWFAX solution to distribute the DOWFAX; and adding 42.23 g/l of 5% Sodium Hydroxide (NaOH) to adjust the pH of the ClO2 solution to a desired pH.

In some embodiments the invention is a method for producing a high concentration chlorine dioxide with improved long-term stability. The method includes 1) adding a molar excess concentration amount of Hydrochloric acid (HCl) to an amount of Sodium chlorite (NaClO2) dissolved in an amount of water; 2) agitating the HCl and NaClO2 until the reaction to form chlorine dioxide (ClO2) is complete; 3) adding an amount of DOWFAX 3B2 (i.e., sodium alkyl diphenyloxide disulfonate, 4) slowly agitating the HCl, NaClO2 and DOWFAX solution to distribute the DOWFAX; and 5) adding an amount of Sodium Hydroxide (NaOH) to the ClO2 solution to adjust the pH to a target value; wherein: the molar excess concentration amount of acid=42.61 g/l 10% HCl; the amount of sodium chlorite=3.20 g/l NaClO2; the amount of DOWFAX=1.50 g/l DOWFAX; the amount of NaOH=42.23 g/l of 5% NaOH; the pH target value approximately 4.5-6.5.

In some embodiments, the delivery device is a spray bottle and the stabilized ClO2 is a sprayable solution; the delivery device is a wipe and the stabilized ClO2 is a solution integrated into the wipe; the delivery device is a tablet and the stabilized ClO2 is integrated into the tablet; the delivery device delivers a laundry detergent and the stabilized ClO2 is integrated into the laundry detergent; the delivery device delivers a deodorizer and the method of producing the ClO2 further comprises adding a fragrance ingredient compatible with ClO2; the delivery device is a cleaning device and the stabilized ClO2 is produced as a concentrate that can be used at full strength or diluted with water.

In some embodiments, the desired pH is 4.5-6.5.

In some embodiments, the ClO2 is a sprayable solution configured to work with a spray bottle; the ClO2 is a concentrated solution configured to be used at full strength or diluted with water prior to use; the method further comprising adding a fragrance ingredient compatible with ClO2 to produce a fragranced solution.

In some embodiments, the process may include a caustic, such as sodium hydroxide to adjust the solution pH. Depending on what acid and the amount of acid that is added to sodium chlorite, the corresponding amount of caustic (NaOH) needed to adjust the pH to stabilize the ClO2 will vary.

(Reference: Chlorine Dioxide by W. J. Masschelein, Ann Arbor Sciences 1979.)

Product Applications/Uses

ClO2 can kill germs, clean, decolorize stains, deodorize, and destroy allergens on hard or soft surfaces for household, commercial and healthcare (including equipment) with bacterial, viral or fungal diseases or contamination.

Laundry

The product may be used in the laundry to sanitize, clean, deodorize or remove stains or destroy allergens on clothes. It could be added through the wash, or added in the rinse cycle (i.e., post cleaning). High efficiency wash machines generally have chambers for various cleaning ingredients. Regular wash machines often have dispensers mounted on the agitator that dispense by centrifugal force to add a fabric softener during the rinse cycle. A dispensing ball or other device in the washing machine that can release the ClO2 after the wash step could be used. There could be injectors or other approaches for all the ClO2 to the wash or post-wash.

The concentration and product form for a laundry/fabric/upholstery product containing ClO2 will vary depending on when it is used, how it is used and intended use. All products may use the core technology of stabilized ClO2. In some embodiments, it could be a two part product that is tailored for the different applications.

Figure 5:
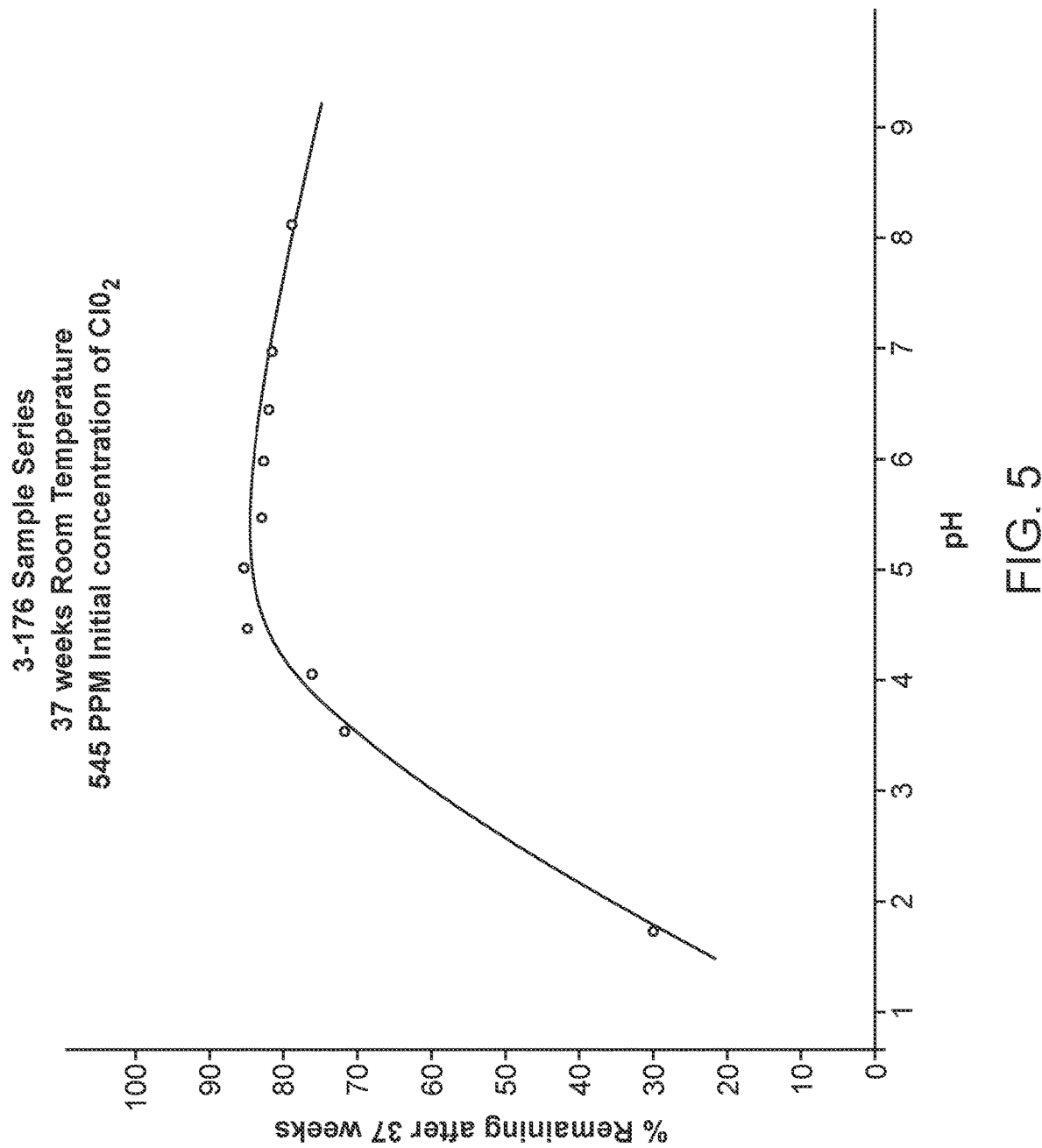
FIG. 5 shows a plot of the percent of ClO2 remaining as a function of pH after 37 weeks.
Figure 6:
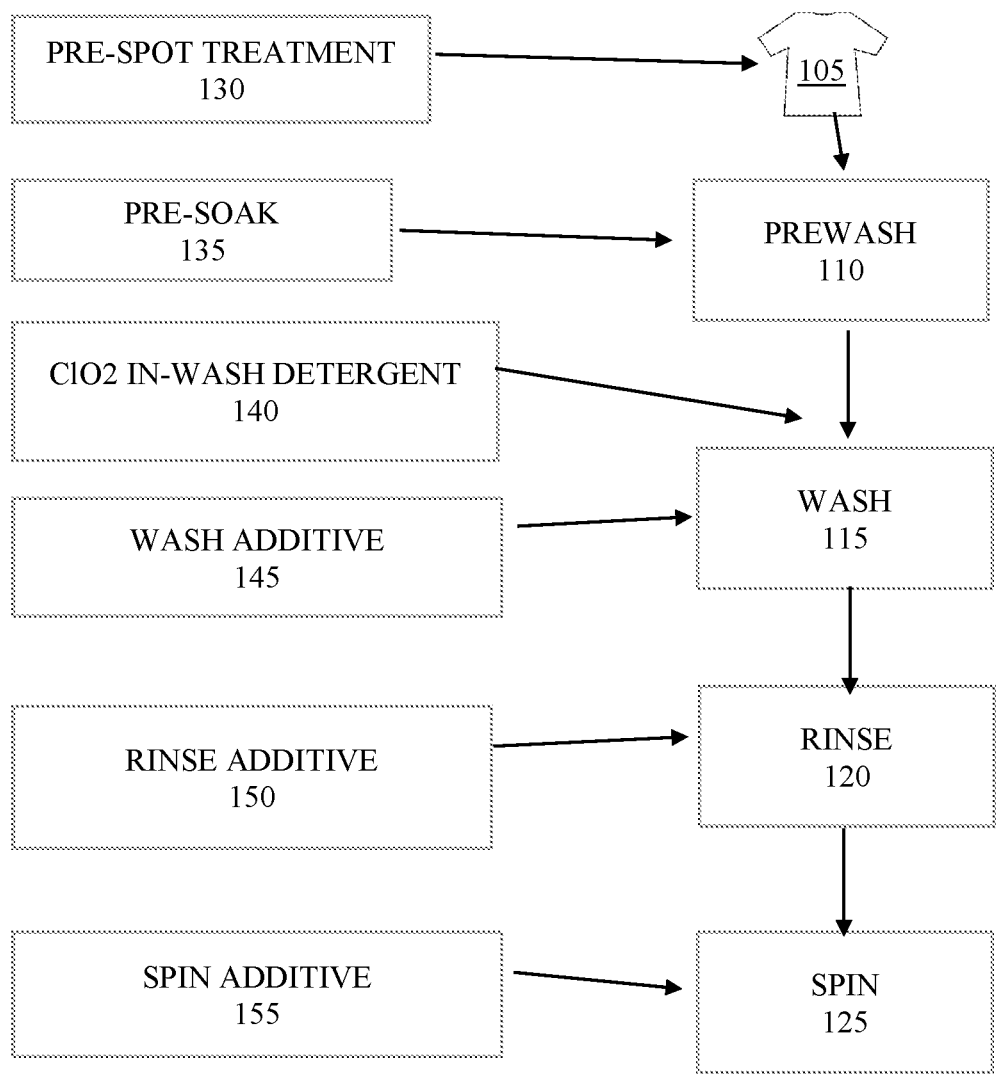
FIG. 6 shows a flow chart using ClO2 with laundry.

FIG. 5 is a flow chart 100 showing various options for sanitizing laundry 105 using ClO2 in a washing machine.

Washing Machine Steps

A typical washing machine cycle includes a number of steps including a prewash 110, wash 115, rinse 120 and spin 125.

Prewash—The prewash step 110 includes filling the washing machine's tub with water, agitate, and spin. Once the pre-wash cycle is complete, the washer will run the regular cycle Washing—During the wash 115, the machine uses agitation to mix the water and detergent, as well as to move the clothing around the tub—and against other clothing—to clean the load.

Rinsing—Rinsing the load 120 is usually a multi-step procedure. First, the soapy water must be removed from the clothing and wash tub. During the latter minutes of the purging, fresh water is sprayed into the tub to rinse the clothing. The rinse cycle uses intervals of spraying and spinning to force the soapy water and detergent out of the washer. A final stage of agitation with plain water is the last step in rinsing and the beginning of the final step: spinning.

Spinning—Spinning 120 is necessary for wringing the clothing, getting it as dry as possible before the end of the wash. Oftentimes, water is sprayed into the wash tub to completely rinse the clothing before it's finally spun to its driest point.

Pre-Wash Cycle—The pre-wash cycle is an extra cycle that can be added at the beginning of most of your washing machine cycles that will fill with water, agitate, and spin. Once the pre-wash cycle is complete, the washer will run the regular cycle.

Sanitizing Laundry Using ClO2

Pre-spot treatment—Stabilized ClO2 may be used for pre-spot treatment 130 of the laundry 105 and may include some surfactant to help with wetting. This product could remove stains and odors. The key is that the concentrations should not be so high so as to cause dye damage if sprayed directly on to fabric with no dilution. If it is used on white laundry, the issue of potential dye damage essentially goes away. Hence, you could have a separate (different) concentration for whites and colored laundry.

Laundry pre-soak—Stabilized ClO2 may be used to pre-soak 135 the laundry 105 in the prewash to soak laundry to remove stains, preclean, deodorize or sanitize prior to washing. It could be done in the washing machine or even in a bucket. The product would be to be concentrated to take in account dilution in the washer. Contact time could vary. Longer contact time translates to improved cleaning, deodorizing, sanitizing benefit. Long contact times are not desired if color or fabric damage occurs.

ClO2 in the detergent as all in one product—Stabilized ClO2 may be included in the detergent 140 to sanitize the laundry 105 during the wash cycle. The concentration of the ClO2 would likely be high given the dilution of the product in the washing machine. Considerable effort would be required to develop a detergent formula with ClO2 present that is stable with good shelf life. This is because many components that are desirable to include in a detergent including fragrance, dyes, brighteners, polymers etc. could have limited compatibility with ClO2. There could be ways of protecting these ingredients from reacting with ClO2, or ClO2 compatible structures could be created. Alternatively, a detergent formula that is void of ClO2 incompatible ingredients could be developed, but this detergent would likely have deficiencies in performance and/or aesthetics.

Laundry additive during the wash—Stabilized ClO2 may be used as a wash additive 145 that is added during the wash cycle to sanitize the laundry 105, similar to the current use of bleach in the wash cycle. The ClO2 may also be a replacement for chlorine bleach or oxy bleach. It could be a concentrated product as typically ½ to 1 cup could be added to the washing machine. It would work in conjunction with the laundry detergent. The concentrations would need to be high in this application because the ClO2 would be diluted and help with cleaning, removing laundry stains, deodorizing and killing bacteria in the wash. The ClO2 would also be consumed by reacting with soils on the laundry and some would likely be consumed reacting with various ingredients in the laundry detergent. Fragrances, dyes and brighteners are some typical detergent ingredient that could have limited compatibility with ClO2.

ClO2 as a rinse additive—Stabilized ClO2 may be used as a rinse additive 150 that is added during the rinse cycle to sanitize the laundry 105. They may also function as a fragrance deodorizer or to deactivate the optical brightener. In this scenario, a deodorizer is extended to include an application here a consumer would purposely want to eliminate the fragrance, and/or to deactivate the fluorescent whitening agents that detergents leave on a garment after washing. For example, hunters generally do not want fragrance or brighteners on their clothes as many game animals have a better sense of smell and better color perception than humans.

ClO2 as a spin additive—Stabilized ClO2 may be used as a spin additive 155 that is added during the spin cycle after the garment is cleaned. It can be added through a dispenser in an HE washing machine or during the spin cycle through a dispenser mounted on top of the agitator on a top leading machine, or added through some other dosing device. The product would be diluted in the washing machine so it would need to be somewhat concentrated but not as high as a laundry bleach since the laundry is generally clean after washing and the bacterial load at that stage of the wash is going to be much lower. Hence the concentration of ClO2 needed during the rinse should be relatively low, say around hundreds of PPM or maybe less than 200 PPM.

Carpet/Rug Cleaning

The ClO2 product may be used for floor and carpet/rug cleaning, sanitizing for pets. It could be a stand-alone spot cleaner or could be put in a carpet cleaning apparatus. ClO2 could be incorporated into a cleaning product, or could be applied as a separate step after cleaning (post cleaning).

Some of the advantages of the ClO2 product include:
1) Better Anti Resoiling (pet)—the ClO2 product is better at removing the scents for pets: (it denatures proteins—breaks them down and breaks down other chemicals that are sensitive to powerful oxidation) so therefore will prevent pets from returning to the same spot since they don't recognize the odor of the chemicals they left there.
2) Dissipates/Dries Quicker—the ClO2 product doesn't leave a residue since it basically reacts then dissipates into the air or evaporates with like water—it will dry at pretty much the same rate as any other water based cleaner it just won't leave behind a residue like many other cleaners.
3) Safe Around Children And Pets—the ClO2 product is food safe so you can feel confident the solution is okay for children and pets to be around.
4) Odor Elimination—the ClO2 product denatures proteins—breaks them down and breaks down other chemicals that are sensitive to powerful oxidation—almost anything that has an odor is prone to oxidation—therefore odors can be eliminated.
5) More Effective Germ Kill—the ClO2 product is among the most powerful oxidizers available and kills bacteria viruses, fungus, and other pathogens.
6) Safe On Carpets And Fabrics—the ClO2 product may be used because most carpets and fabrics today have dyes that are resistant to oxidation from cleaners.
7) Environmentally Friendly—the ClO2 product does not leave a residue nor does it create chlorinated byproducts (a carcinogenic residue) like other germ kill products such as sodium hypochlorite.

Floor Cleaning

A ClO2 product could be used full strength, or a concentrated product can be diluted to clean floors. The ClO2 product could be applied after cleaning the floor as a separate step i.e., post cleaning. It could be a stand-alone floor cleaner product or could be added to a cleaning formula provided that the ClO2 is compatible with the formula.

The product could be applied with a device such as a Swiffer™ (a device that dispenses a liquid as you mop). This device could also include the floor cleaner. Large floor cleaning machines are often seen to clean hallways in commercial buildings/hospitals etc.

Hard Surfaces

Used full strength or diluted for use on toilet bowl, sinks, cutting boards, highchairs, baby/kids toys, pacifiers, upholstery, kitchen ware. floors, laundry, etc.

Decontamination of Clothing or Equipment

ClO2 could be used for decontamination of hazmat suits or equipment. It could be used on farming equipment etc. to prevent transfer of bacteria/pathogens from one crop field to another.

Fruit and Vegetable Wash

A concentrated product could be diluted and used as a wash for fruits and vegetables. Fruits and vegetables could be washed just as they are harvested, or could be washed in the consumer's home before eaten. Reducing molds could reduce spoilage and extend the storage of fruits and veggies.

A product may be used in agriculture and other plants: especially crops, e.g., sugar cane, rice, with fungal, viral and bacterial diseases;

Personal Care for Humans

The product may be used on "human surfaces" to control bacterial, viral and fungal diseases or contamination, e.g., mouthwash, gargle, rinse or other for throat, nose, douches skin, wounds or other internal uses.

The formulation may include the addition of salt (NaCl) pH adjusted and no surfactant—also could be just ClO2 solution.

ClO2 in either a concentrate or ready to use product could be used in applications such as; mouth wash, body wipe, wound care, treatment for skin infections or acne, and a potential remedy for poison oak. The concentration of ClO2 would vary depending on the application. We could combine ClO2 on a wipe substrate to be used on skin, as well as, on hard surfaces.

Decontamination

The product may be used for decontamination before transportation (use as foot wash for shoes, boots, equipment, tires, etc.) when travelling between countries or sensitive agricultural or wildlife areas; e.g., prevent the spread of fungal or other contamination to the sensitive frog populations of the world by decontamination of the boots and equipment of the biologists studying the populations at various locations.

Animals

The product may be used with animals both domesticated and wild to prevent fungal, viral and bacterial diseases.

The product may be used for animal wounds and skin disease treatments as well as hoof wash and other treatments including decontamination. Cleaning animal stalls could help prevent fungal, viral, and bacterial infections.

Swimming Pools

ClO2 could have applications in swimming pools and spas where ClO2 could be an alternative to sodium hypochlorite or sodium hypobromite. Both ClO2 and hypochlorite are sensitive to UV light. There are situations where a fast acting biocide and fast degrading biocide may be desirable such as in a pool shock treatment. In such a treatment, a high dose of biocide is added to kill algae but would allow you to swim in a relatively short time afterwards.

Mold/Mildew

ClO2 kills mold and the mold can be decolorized by ClO2. Hence, you can kill mold and remove the dark mold stain with the same product. Some agents such as alcohol and high levels of quaternary ammonium compounds can/will kill mold but do not decolorize it.

Teeth Whitening

As previously discussed, the product may be used as a mouth wash/oral rinse etc. In addition, a ClO2 product could possibly be used to whiten teeth.

ClO2 Components

Acids

Any suitable acid may be used in the process disclosed. We define suitable as an acid that reacts with NaClO2 to form ClO2 and is also compatible with ClO2. Such acids generally have a pKa less than about 5. For example, but not limited to, hydrochloric acid, sulfuric acid, nitric acid, perchloric acid, malonic acid, citric acid, sulfamic acid, succinic acid, and oxalic acid.

Acids may be moderate to strong acids that are capable of reacting with sodium chlorite to form ClO2. The strongest acids are "mineral acids" which completely dissociate in aqueous solution. Common examples of strong acids are hydrochloric acid, sulfuric acid, and nitric acid. These are characterized as having pKa s<1. Strong acids react very quickly with sodium chlorite.

Moderately strong acids include many organic acids. Examples include, citric acid, sulfamic acid, succinic acid, and oxalic acid. These are characterized as having pKa values less than about 5. The acid needs to react with sodium chlorite to form ClO2. If the pka is too high, the reaction will not occur or will be very slow. Generally, the lower the pKa, the stronger the acid and the faster the reaction with sodium chlorite.

Combination of Acids

The reaction of NaClO2 with an acid is used to produce ClO2. The acid can be mineral acid or organic acids. Mineral acids have pKa<1. Organic acids have a pka<5. Adding excess acid, which is the amount required by the stoichiometry of the reaction will speed up the reaction and maximize the conversion of chlorite to ClO2.

The process may be done using a combination (mixture) of acids rather than just using one acid.

In some embodiments, formulations without the addition of any ingredients other than the ClO2 that is produced may be desirable.

Surfactants and Other Formula Ingredients

Surfactant and other adjuncts can be added to the basic solution to create a range of products. Surfactants help facilitate cleaning and wetting of surfaces to improve the micro efficacy of chlorine dioxide. The key criteria are that the surfactants must be reasonably compatible with ClO2 and other potential formula ingredients, and must function in the particular product. The Examples shown above use DOWFAX 3B2 (i.e., sodium alkyl diphenyloxide disulfonate) for the surfactant. DOWFAX 3B2 was chosen for its compatibility with ClO2. The present invention is not limited to just DOWFAX 3B2 for the surfactant.

The surfactant can be added at any time during the production of ClO2. It can be added to solution before the acid is added to chlorite. It can be added to solution after the ClO2 is formed, or it can be added after the pH is adjusted. We could also have a mixture of surfactants.

Examples of Acid and Acid Mixes

In all these examples,
1. The surfactant was added to solution with sodium chlorite, before the acid was added. After the acid was added, the reaction ran for several minutes to generate chlorine dioxide.
2. The molar ratio of acid to chlorite in all these samples was 3.3/1. Only the type of acid was changed. (The target level of ClO2 was ~550 PPM based on titration.
3. The reaction ran for 40 minutes. After which, sodium hydroxide was added to adjust the solution pH to pH~6.)
4. Having some organic acid or the sodium salt of the organic acid can form a pH buffer which could be an optional ingredient. The organic acid could be part of the acid used to react with chlorite to generate ClO2, or a small amount of the organic acid or its sodium salt could be added during the pH adjustment phase to create the pH buffer. The key criteria are the acid or sodium salt of the acid be compatible with ClO2 and that the pKa of the acid generally be within about 1 pH unit of the formula pH to create a buffering effect. The amount the buffer which should added to control the formula pH should be 0-0.5 Wt Percent of the formulation.

Below are samples of chlorine dioxide-based formulation using acid and acid mixes and adjusting to a pH~6.

Sample 1—HCL

| Component | Wt (g) |
| --- | --- |
| NaClO2 | 1.28 |
| Dowfax 3B2 | 1.00 |
| H2O | 980.67 |
| HCl (10%) | 17.05 |
| Total | 1000.0 |

1. 10% HCl 17.05 g added to the combination of NaClO2, DOWFAX 3B2, and water (Total 1000 g)
2. pH of solution after the reaction was 1.53.
3. A pH meter probe was put into the solution and 5% NaoH was added until pH 6.
4. The amount of 5% NaOH required was 35.19 g to adjust to pH-6.

Sample 2—Citric Acid Monohydrate

| Component | Wt (g) |
|---|---|
| NaClO2 | 1.28 |
| Dowfax 3B2 | 1.00 |
| H2O | 994.50 |
| Citric acid monohydrate | 17.05 |
| Total | 1000.0 |

1. pH of solution after adding citric acid pH 2.60
2. Amount of 5% NaOH needed to adjust to pH 6 was 31.0 g With citric acid, the reaction to produce ClO2 is slower than with equivalent molar concentration of mineral acid. Utilizing an organic acid such as citric or oxalic acid, which have pKa values higher than a mineral acid, increases the reaction time to produce ClO2. Increasing the concentration of the organic acid will speed the reaction to produce ClO2. However, the corresponding amount of caustic required to adjust the pH to the desired value to improve the stability of the ClO2 will also increase.

Using an organic acid or its corresponding sodium salt with a pKa value close to the desired final product pH will also have the benefit of buffering the pH i.e., help keep the pH constant.

Generally, the pH and the pKa should be about 1 pH unit difference to have a buffering effect. The pKa of citric acid are 3.08, 4.74 and 5.40. Having some organic acid present with a pKa close to the formula pH will help maintain the pH. For a formula example at pH~6, citric acid will provide a buffering effect. The overriding requirement is compatibility of the acid and ClO2. A small amount of citric will help maintain the pH. The addition of 0-0.5 Wt percent of citric acid or sodium citrate percent should provide a good buffering effect with the pH adjusted formula. However, since the stability of ClO2 is good over a broad range as shown in FIG. 5 b, the addition of a buffering agent is optional.

Sample 3-50%/50% Blend of HCl and Citric Acid Monohydrate

| Component | Wt (g) |
|---|---|
| NaClO2 | 1.28 |
| Dowfax 3B2 | 1.00 |
| H2O | 987.60 |
| Citric acid monohydrate | 1.63 |
| HCl (10%) | 8.52 |
| Total | 1000.0 |

1. The pH after the reaction was 1.88. This reaction was slower than using HCl alone but faster than citric acid monohydrate alone.
2. Adjusted the pH to ~6 using 33.2 g of 5% NaOH.

Adding a small amount of an organic acid or its sodium salt after the ClO2 is produced reaction but prior to adjusting the pH will function as a buffer provided that the formula pH and pka of the acid are within about 1 pH. It may not be necessary to use the organic acid to produce the ClO2 but instead add either the acid or its sodium salt during the pH adjustment. The citric acid or sodium citrate could be added just before adjusting the pH to get the buffering effect if desired.

Other Adjuncts

Gum thickeners can be added to thicken the product to improve contact time on a vertical surface or potentially as in a hand sanitizer. For example, gum thickeners may include, but not limited to, xanthan gum, Kelzan AP-AS (from CP Kelco), Keltrol (from CP Kelco) or other suitable gum thickener. The key is that the adjuncts must be reasonably stable with chlorine dioxide. The benefits of proper pH choice also apply to the addition of adjuncts. We are not limited to just these two ingredients. Optimizing the pH will improve stability of formula containing the desired adjuncts.

Other Components

Other formula components are possible including fragrances, dyes, enzymes, cleaning agents, anti-redeposition agents, wipe substrates, brighteners etc. Additional oxidant stable ingredients e.g., scents/fragrance ingredients, foaming or de-foaming ingredients, may also be added. The choice of these other components depends on the product application. A key feature is that they should be compatible with ClO2.

Concentrated Product

A concentrated product could have applications such as a floor cleaner, general cleaner/deodorizer, use in toilet bowl, or in laundry applications. The concentrated product is a product that may be used full strength or be diluted prior to use. The product is prepared using a stabilized formula and then diluted by adding additional water or adding the concentrated formula to water. An example of a concentrated product and how one is used, is Pine-Sol™. Pine-Sol™ can be used full strength or diluted. The standard dilutions would apply. i.e., add product to an equal amount of water would dilute it by 50% etc. The concentrate could be a diluted refill for a spray product.

It would also be possible to make a concentrate two-part product where the acid and chlorite are separated until they are combined to react. Since there is no ClO2 produced until acid and chlorite react in a two-part product, the stability issues of ClO2 could be avoided. After mixing the acid and sodium chlorite, the resulting ClO2 would have a limited lifetime or could be further stabilized by adjusting its pH.

The procedure to prepare a ClO2 concentrate is the same as discussed above. We would add excess acid to sodium chlorite and wait for the reaction to produce ClO2 to go to completion. Surfactant could be present either before or after the reaction of acid and chlorite. Then adjust the pH so that the product is in the pH in the range that provides improved stability. The concentrate is then ready for use.

The concentration of the chlorine dioxide and the surfactant would be higher in the concentrated product to allow for dilution so that the diluted product will still have a concentration to be effective. Higher concentration of ClO2 may be used to sanitize or disinfect while a lower concentration of ClO2 in the diluted form may be good for general cleaning and deodorizing.

The concentrated product should be safe to use and have a suitable shelf life for storage.

In some embodiments the product may include other ingredients, such as fragrance, dyes, or thickeners, etc. to change the aesthetics or the form of the product or even change other performance attributes. In some embodiments gum may be added to make a gel product. These other embodiments should be chosen based on compatibility with ClO2 for a suitable shelf life, as well as, for its intended function.

Dilution—Preparation of Finished Product

Deionized water should be used to prepare or dilute the Solution during production of the finished product. The pH of the finished product should be adjusted to improve stability and/or to achieve the desired product pH. If the product is required to have a specific pH, the overall stability of the ClO2 could subsequently be affected. It is therefore preferred to have the product pH fall within the pH range that promotes the improved stability.

ClO2 Product Delivery

It is envisioned that the ClO2 product be delivered in many different forms using many different devices or applicators for delivery, depending on the application. Below are some non-limiting examples.

Sanitizer or Disinfectant—For hard surfaces, the ClO2 product may be packaged in a spray bottle or package of wipes. For hand sanitizer, the ClO2 product be in a squirt or pump bottle. For soft surfaces, the ClO2 product may be provided in a concentrated solution either at full concentration or diluted that can be used/applied with a cleaning machine, such as a carpet cleaner, vacuum, floor cleaner, steam cleaner, or other cleaning/disinfection machine.

Floor Cleaner—The ClO2 product may be provided in a concentrated solution that can be used either at full concentration or diluted, such as Pine-Sol™. The ClO2 product may be applied using a cleaning machine, such as a hard floor cleaner or sweeper capable of delivering fluids to the floor.

General cleaner/deodorizer—The ClO2 product may be provided in a spray bottle, like Lysol Bathroom Cleaner™, or disinfecting wipes like Clorox™ Wipes™.

Toilet—The ClO2 product may be provided in a tablet form to drop-in the bowl or put in the toilet tank for each flush, like Clorox™ tablets. The tablets may be different concentrations, such as the drop-in bowl tablet may have a higher concentration than the tank tablet.

Laundry—The ClO2 product may be mixed in a laundry detergent; or may be a separate solution additive, like Lysol™ Laundry Sanitizer Additive, that is added through the wash, or added in the rinse cycle; or as beads that are thrown in the wash, like Downy™ Fresh Scent Booster Beads; or as a ball or other device in the washing machine that could release the ClO2 after the wash step.

EXAMPLES

For example, sodium chlorite (NaClO2) and hydrochloric acid (HCl), shown in Formula (1).

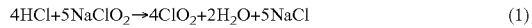

4HCl+5NaClO2→4ClO2+2H2O+5NaCl     (1)

It is generally desirable to have an excess of HCl because it helps speed the reaction and maximizes the conversion of NaClO2 to ClO2. The resulting pH of samples typically produced this way is pH<2.

Example 1

A first batch of ClO2 (3-134), prepared as described in Formula (1) was split into two subsamples. The pH of one subsample was adjusted to pH 3.66 with Sodium Hydroxide (NaOH) (3-134A) and the other subsample was not adjusted and was pH 1.70 (3-134B). A second batch of ClO2 (3-131), prepared as described in Formula (1) at a lower concentration of ClO2 split into two subsamples. The pH of one subsample was adjusted to pH 3.62 (3-131A) and the second subsample was not adjusted and was pH 1.96 (3-131B). The samples were stored in closed amber glass jars. At various times, aliquots were removed and the ClO2 was assayed using the iodometric titration.

FIG. 1 is a plot of the ClO2 concentration vs. time for the samples. As seen in the plot, increasing the pH results in a much more stable product, i.e., slower loss of the ClO2 concentration over time. Raising the sample pH also has the key benefit of preventing the initial rapid drop in ClO2 typically seen in the first few days after synthesis of ClO2. Preventing this initial drop in activity is more cost effective for manufacturing and makes it easier to achieve the desired concentration.

Assay for ClO2

Iodometric titration is a well-known analytical technique that is used to determine the concentration of sodium hypochlorite. Another method which may be used is a spectrophotometric determination using a meter, such as a Hach meter, that has programmed analysis for ClO2. The value calculated from titration may be different than what you get using the Hach meter but either assay method can be used. The user should just be consistent on how the samples are assayed.

Example 2

Figure 2:
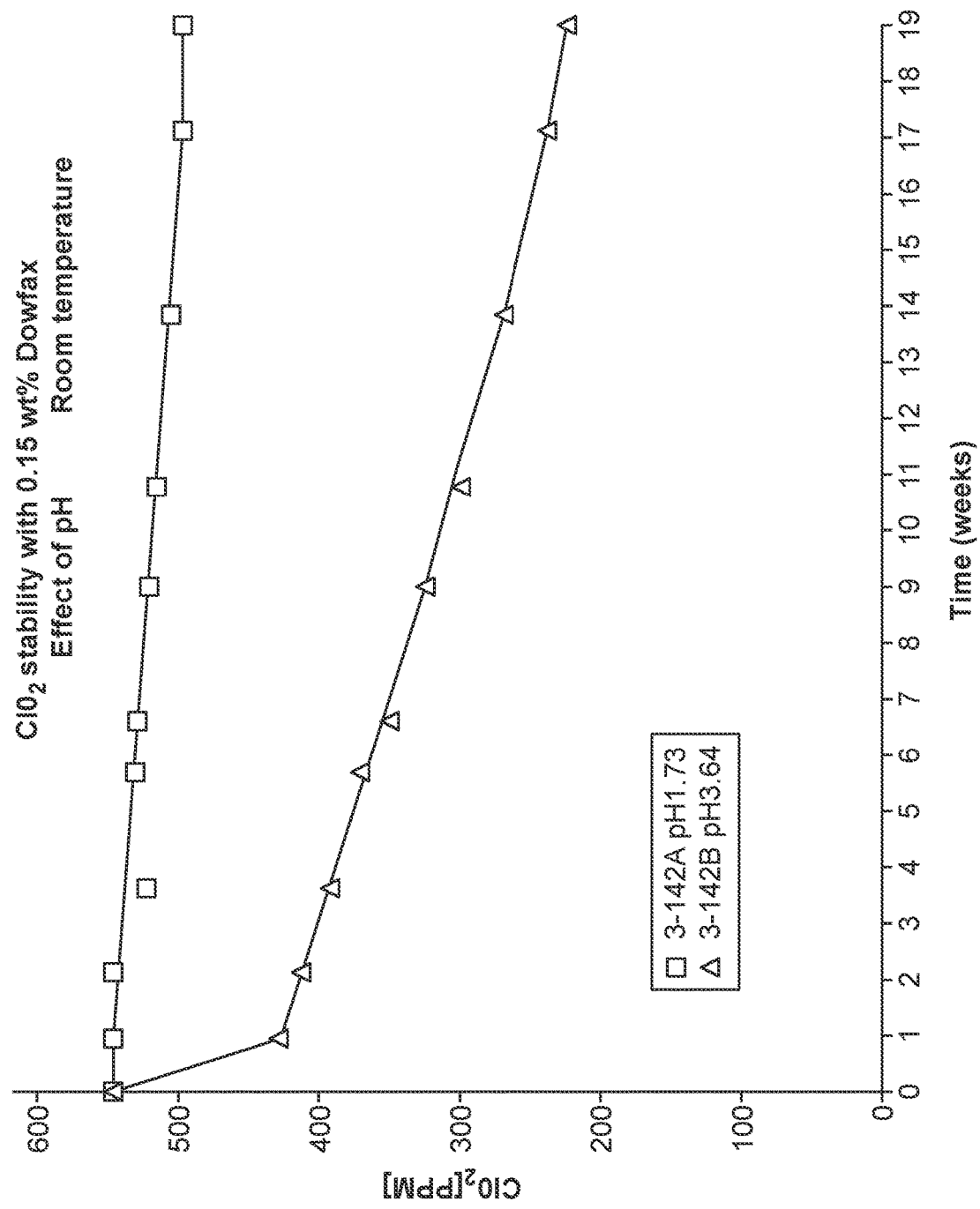
FIG. 2 shows a stability profile of chlorine dioxide and surfactant compositions with differing pH levels vs. time.

FIG. 2 shows a stability profile of another set of samples with surfactant added (3-142), in this case, DOWFAX 3B2 (i.e., sodium alkyl diphenyloxide disulfonate) surfactant. The ClO2 (3-142) was prepared as described in Formula (1) and split into two sub samples. The pH of one subsample was adjusted to pH 3.64 (3-142B) with Sodium Hydroxide (NaOH) and the other subsample was not adjusted and was pH 1.73 (3-134A). Both samples were stored in closed amber glass jars. At various times, aliquots were removed and the ClO2 was assayed using the iodometric titration. FIG. 2 is a plot of the ClO2 concentration with vs. time. This plot again shows increasing the pH to 3.64 results in a much more stable product than the pH 1.73 sample, i.e., slower loss of the ClO2 concentration over time.

Example 3

Figure 3:
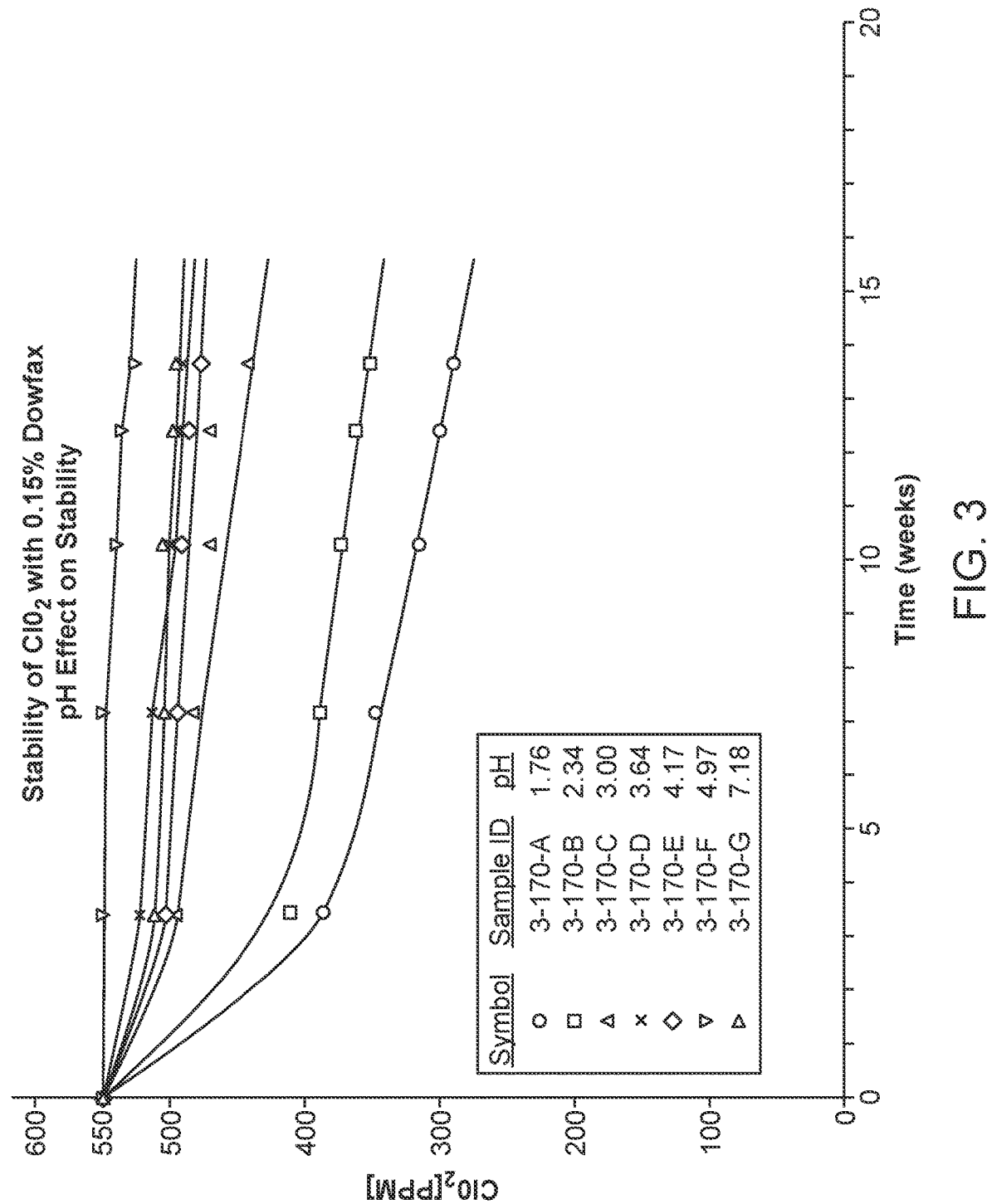
FIG. 3 shows a stability profile of chlorine dioxide and surfactant compositions with differing pH levels vs. time.

FIG. 3 shows a stability profile of another set of samples with surfactant added (3-170), in this case, DOWFAX 3B2 (i.e., sodium alkyl diphenyloxide disulfonate)surfactant. FIG. 3 is similar to FIG. 2 but with samples at a broader range in pH. The ClO2 with surfactant was prepared as described and split into seven subsamples. The pH of the first subsample 3-170A was not adjusted and was pH 1.76. The pH of the other subsamples 3-170B to 3-170G were adjusted with Sodium Hydroxide (NaOH). All samples were stored in closed amber glass bottles.

3-170 A pH 1.76
3-170B adjusted to pH 2.34
3-170C adjusted to pH 3.00
3-170D adjusted to pH 3.64
3-170E adjusted to pH 4.17
3-170F adjusted to pH 4.97
3-170G adjusted to pH 7.18

FIG. 3 shows the effect of pH on stability. The graph shows raising the pH in subsamples 3-170B to 3-170G improved stability. However, sample 3-170G with pH 7.18 was not as stable as the samples as pH 4.97 (3-170F), suggesting there may be an optimal pH range for stability where pH~5 appears to have better stability than pH 3.6.

Example 4

Figure 4:
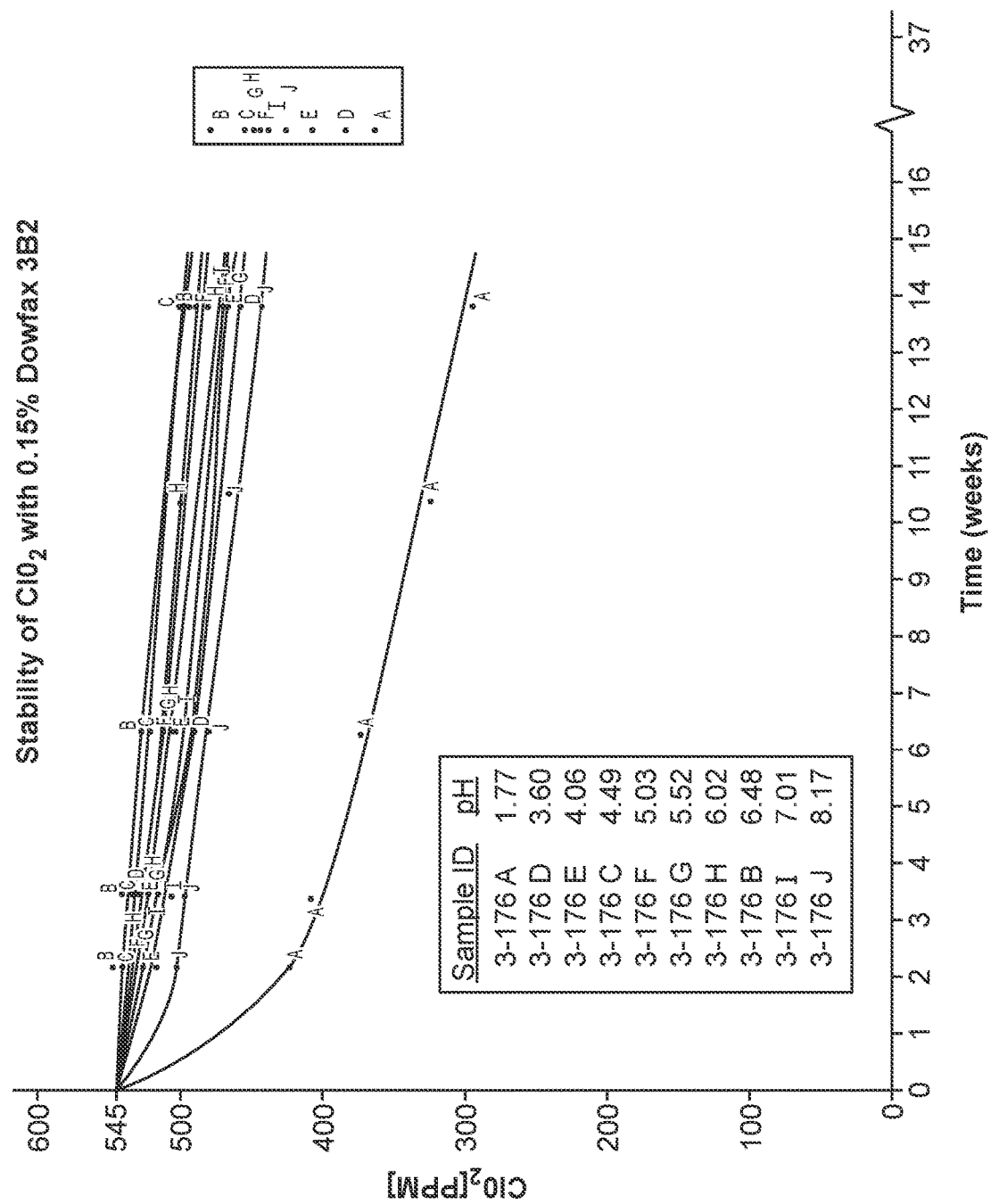
FIG. 4 shows a stability profile for a series of samples with DOWFAX 3B2 (i.e., sodium alkyl diphenyloxide disulfonate).

FIG. 4 shows the stability profile for yet another series of samples with DOWFAX 3B2 (i.e., sodium alkyl diphenyloxide disulfonate) (Sample series 3-176A-J). The same procedure was used in preparing the samples. A large sample batch was prepared which was then split into ten sub samples. The pH of the subsamples was adjusted by addition of sodium hydroxide. The samples were stored at room temperature in closed amber glass bottles. At various times, aliquots from the subsamples were removed and the concentration of ClO2 was assayed using an iodometric titration. The sample pH's were checked and adjusted if necessary, to the original sample pH. The initial concentration of ClO2 was 545 PPM. Table A shows the concentration of ClO2 and the corresponding calculated percent remaining based on the initial concentrations at 6, 14 and 37 weeks.

TABLE A

| | 6 weeks | | 14 weeks | | 37 weeks | |
|---|---|---|---|---|---|---|
| Sample pH | ClO2 PPM | Percent Remaining | ClO2 PPM | Percent Remaining | ClO2 PPM | Percent Remaining |
| 1.77 | 377 | 69.2 | 298 | 54.7 | 162 | 29.8 |
| 3.60 | 493 | 90.4 | 460 | 84.4 | 386 | 70.8 |
| 4.06 | 508 | 93.2 | 460 | 86.1 | 410 | 75.3 |
| 4.49 | 526 | 96.5 | 503 | 92.3 | 459 | 84.2 |
| 5.03 | 515 | 94.5 | 487 | 89.4 | 458 | 84.1 |
| 5.52 | 516 | 94.7 | 484 | 88.8 | 440 | 82.4 |
| 6.02 | 520 | 95.4 | 483 | 88.6 | 451 | 82.8 |
| 6.48 | 528 | 96.9 | 496 | 91.0 | 450 | 82.6 |
| 7.01 | 503 | 92.3 | 473 | 86.8 | 442 | 81.1 |
| 8.17 | 482 | 88.4 | 447 | 82.0 | 427 | 78.3 |

Sample 3-176 A-J

FIG. 5 shows a plot of the percent of ClO2 remaining as a function of pH at the T=37-week data using the data from Table A. The profile shows the improved stability resulting from increasing the samples pH with the optimal pH at ~5 consistent with the data shown in FIG. 4.

General Instructions

All chemicals are used without further purifications. All samples bottles used were amber and appropriately labeled. Each container was rinsed with deionized water before reusing.

All processes and reactions are carried out at room temperature not exceeding (22° C.) unless otherwise specified.

The present invention may be used for various products, including, for example, a surface disinfectant or sanitizer. While the present application discloses embodiments for a surface disinfectant, it is contemplated that the same processes, methods, and solutions may be used for the other products.

Basic Solution

Below is one example of chlorine dioxide based final formulation with improved stability.
1 Hydrochloric acid solution (HCl).
2 Sodium chlorite (NaClO$_2$).
3. Sodium Hydroxide (NaOH)
4 Deionized water (H$_2$O).

Chlorine Dioxide Composition Products Types

Table 1 below shows a base solution composition used for disinfectant/sanitizer solution depicted in FIG. 1 3-134 A/B. As described above, NaClO2 is dissolved in deionized water. The aliquot of 10% HCl was added. The mixture is stirred and allowed to react for 15 minutes. The batch was then split into two subsamples.

TABLE 1

| | pH adjusted Base Solution | | | |
|---|---|---|---|---|
| Product type | 1 | 2 | 3 | 4 |
| Disinfectant | 34.10 g 10% HCl | 2.56 g | See below | 1963 g H2O |

32 g of 5% NaOH was added to a 1 liter sample of 3-134B with a resulting pH of 3.66

32 g of H2O was added to Samples 3-134A to insure the identical volume both samples. The pH of 3.134 A was 1.70.

Surfactant Solution

Below is one example of chlorine dioxide-based formulation having a surfactant with improved stability.
1 Hydrochloric acid solution (HCl).
2 Sodium chlorite (NaClO$_2$).
3. Surfactant (for example, DOWFAX 3B2).
4. Sodium Hydroxide (NaOH)
5 Deionized water (H$_2$O).

Table 2 below shows some example ranges as used in FIG. 2.

TABLE 2

| | pH adjusted with Surfactant (g/liter) | | | | |
|---|---|---|---|---|---|
| Product type | 1 | 2 | 3 | 4 | 5 |
| Disinfectant | 17 g 10% HCL | 1.28 | 1.5 | 16 g 5% NaOH | 980 |

Chlorine dioxide (ClO$_2$) decomposes more quickly when exposed to light, is temperature sensitive and it reacts with many organic compounds. Proper shielding from light and clean production facilities and handling procedures, and material purity are essential to improve stability and avoid unwanted reactions with organic contaminants during production.

The resulting concentration of chlorine dioxide can be tailored to meet the desired biocidal performance. As with many biocidal products, the product of the concentration and the contact time I.e. cxt=constant. As a simplistic approximate relationship, doubling the concentration can result in a reduction of concentration to yield a similar degree of micro efficacy.

Table 3 shows typical ranges of ingredients to produce sanitizer/disinfecting/deodorizing solutions.

TABLE 3

| Component | Wt Percent |
|---|---|
| NaClO2 | 0.0050-0.90 |
| HCl | 0.0016-11.00 |
| Surfactant | 0.00-3.00 |
| NaOH | 0-0.90 |
| H$_2$O | balance |
| Total | 100.0 |

It is understood that a practical method of making a very dilute solution of chlorine dioxide, at concentrations as low as 1 PPM, can be prepared by further dilution of a more concentrated solution using deionized water. The lower limit represents the stoichiometric limit from Formula 1.

Higher Product Concentration

The examples described above had a starting concentration of about 550 PPM ClO2. The present invention also contemplates making a solution of chlorine dioxide with higher concentration 1200-1300 PPM having a pH 4.5-6.5 for various applications. The upper limit of HCl assumes a several fold molar excess of HCl to speed the reaction rate.

Table 4 shows an example of ingredients for producing a product having about 1250 PPM ClO2 and pH 5.91.

TABLE 4

| Component | Wt Percent or | Grams per Liter |
| --- | --- | --- |
| NaClO2 | 0.320 | 3.20 g/l |
| 10% HCl | 4.261 | 42.61 g/l |
| Dowfax 3B2 | 0.150 | 1.50 g/l |
| NaOH | 4.230 | 42.23 g/l |
| H2O | balance | balance |
| Total | 100.0 | 100.00 |

A batch of the 1250 PPM ClO2 was prepared as described in Table 4 and was split into two subsamples. The pH of one subsample was not adjusted and was pH 1.50 and the second subsample adjusted using 42.3 gm of 5% NaOH to a pH 5.91.

The sample of the adjusted pH 5.91 and the non-adjusted pH 1.50 formula were titrated at various times out to 8 months. At 8 months, the control non-adjusted pH 1.50 sample lost 92% (8% remaining) and the adjusted pH 5.91 sample lost 27% (74% remaining) activity.

The 550 PPM ClO2 initial concentration losses after 8 months was ~15%. Hence, the percentage of loss increases with concentration even with pH adjusted samples. The limit of how high a concentrated product can be made depends on the amount of acceptable concentration loss over time. It appears that a high concentrated product may be acceptable if the time period for use is shorter than a lower concentrated product. This may also depend application of the product. While the above sample was 1250 PPM, higher concentrations are also contemplated.

Production Process

The production/manufacturing for the ClO2 based solution should follow general manufacturing guidelines that are typically followed in the production of hypochlorite or peroxide containing based products. All contact surfaces in the production equipment, filling and line and packaging should be in good condition. They must/should be emptied and thoroughly rinsed so as to prevent cross contamination prior to use. Such practices are generally followed in the production of hypochlorite containing products or other products where contamination is undesirable/not tolerated.

Preferably, the entire production process for the solution would be conducted under clean room conditions, in order to minimize the possibility of contamination of the solution by environmental contaminants, such as airborne particles. All contact surfaces, including without limitation surfaces of production equipment, filling equipment and packaging, should be thoroughly cleaned of contaminants prior to use.

Batch Process for Preparation of Chlorine Dioxide

Ranges for the amounts of the Solutions to be used for each embodiment are shown above.

1. Prepare the mixing vessel by decontaminating the container with chlorine dioxide followed by a rinse with deionized water. If the container is used regularly, the container may be rinsed with only deionized water.
2. Add deionized water corresponding to size of the batch followed by the sodium chlorite. Allow the sodium chlorite to completely dissolve. Agitate the sodium chlorite solution.
3. Add the hydrochloric acid to the sodium chlorite solution. After the hydrochloric acid is added, the vessel should be loosely capped to allow the release of any gas that may have formed in the container. The amount of gas formed will vary depending on the concentrations of hydrochloric acid and sodium chlorite present.
4. Allow the acid-chlorite mixture to react for at least 10-30 minutes with slow agitation.
5. Add the surfactant. Mix or slowly agitate to distribute the surfactant.
6. Adjust the pH with sodium hydroxide solution to achieve the target pH for a stable solution. It is recommended that a pH meter be used to monitor the pH.
7. Store samples in sealed opaque/dark containers.

In the procedure described above, it is also generally acceptable to add the surfactant to the dissolved sodium chlorite before adding the HCl. Allow the chlorite-surfactant-acid mixture to react with slow agitation and then adjust the pH with sodium hydroxide. Alternatively, the surfactant can be added after the pH is adjusted.

Continuous Process Preparation of Solution

Below shows one embodiment of a continuous process for preparing chlorine dioxide Surface Disinfectant.

A. Turn on the water pump in the reactor unit and adjust the deionized water to the desired feed rate.

B. Turn on the chemical solutions feed pumps and set the feed rates to the desired percentage of hydrochloric acid, sodium chlorite and surfactant (optional). The sodium hydroxide can be added downstream to adjust the pH.

C. Assure proper mixing of the water and chemicals.

It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth here below not be construed as being order-specific unless such order specificity is expressly stated in the claim.

The invention claimed is:

1. A laundry sanitizer containing chlorine dioxide to sanitize, clean, deodorize or remove stains or destroy allergens on clothes, the method for producing the laundry sanitizer comprising:

adding an amount of an acid solution to an amount of sodium chlorite that is dissolved in water;

agitating the acid solution and sodium chlorite to mix the chemicals for a first time period allowing the chemical to react to completion resulting in chlorine dioxide solution; and adding an amount of sodium hydroxide to adjust the pH of the resulting chlorine dioxide solution to a target value.

2. The laundry sanitizer of claim 1, further comprising a washing machine cycle including a prewash cycle, wash cycle, rinse cycle or spin cycle, wherein the laundry sanitizer is added during the prewash cycle, wash cycle, rinse cycle or spin cycle.

3. The laundry sanitizer of claim 1, further comprising a laundry detergent solution, wherein the laundry sanitizer is added to the laundry detergent solution resulting in an all in one laundry detergent and laundry sanitizer.

4. The laundry sanitizer of claim 1, further comprising adding an amount of caustic to adjusting the pH, wherein the amount of caustic needed to adjust the pH will vary depending on what acid and the amount of acid that is added to sodium chlorite.

5. The laundry sanitizer of claim 1, wherein the acid solution is selected from the group consisting of hydrochloric acid, sulfuric acid, nitric acid, perchloric, phosphoric, acetic acid, citric acid, sulfamic acid, succinic acid and oxalic acid.

6. The laundry sanitizer of claim 1, wherein the acid solution is a combination of at least two acid solutions.

7. The laundry sanitizer of claim 6, further comprising adding an amount of caustic to adjusting the pH, wherein the amount of caustic needed to adjust the pH will vary depending on what acid and the amount of the at least two acid solutions that are added to sodium chlorite.

8. The laundry sanitizer of claim 1, further comprising the addition of 0 to 0.5% of an organic acid or its alkali metal salt to the solution containing chlorine dioxide where in the solution pH and the pka of the organic acid are within about 1 pH unit so that the organic acid functions as a pH buffer to maintain formula pH.

9. The laundry sanitizer of claim 1, further comprising adding surfactant or other formula adjuncts.

10. The laundry sanitizer of claim 1, wherein the pH target value is 2.3-8.2.

11. The laundry sanitizer of claim 1, wherein the pH target value is 3.6-7.5.

12. The laundry sanitizer of claim 1, wherein the pH target value is 4-6.5.

13. The laundry sanitizer of claim 1, wherein pH adjusted chlorine dioxide solution is produced using:
the amount of acid solution=17 g of acid solution; which is added to
the amount of sodium chlorite=1.28 g of sodium chlorite dissolved in deionized water
After agitating the mixture for the first time period to completion, add
the amount of sodium hydroxide=36.2 g of sodium hydroxide.

14. The laundry sanitizer of claim 1, wherein pH adjusted chlorine dioxide solution is produced using:
the amount of acid solution=17 g of the at least two acid solutions; which is added to
the amount of sodium chlorite=1.28 g of sodium chlorite dissolved in deionized water;
after agitating the mixture for the first time period to completion, add
the amount of sodium hydroxide=36.2 g of sodium hydroxide.

15. A laundry sanitizer containing chlorine dioxide to sanitize, clean, deodorize or remove stains or destroy allergens on clothes, the method for producing the laundry sanitizer comprising:
adding an amount of a combination of at least two acid solutions to an amount of sodium chlorite dissolved in deionized water;
adding an amount of one or more surfactants to the solution; and
adding an amount of sodium hydroxide to adjust the pH of the resulting chlorine dioxide solution to a target value;
where the pH is adjusted after the reaction to generate ClO2 in solution has gone to completion.

16. The laundry sanitizer of claim 15, further comprising a washing machine cycle including a prewash cycle, wash cycle, rinse cycle or spin cycle, wherein the laundry sanitizer is added during the prewash cycle, wash cycle, rinse cycle or spin cycle.

17. The laundry sanitizer of claim 15, further comprising a laundry detergent solution, wherein the laundry sanitizer is added to the laundry detergent solution resulting in an all in one laundry detergent and laundry sanitizer.

18. The laundry sanitizer of claim 15, further comprising agitating the combination of at least two acid solutions and sodium chlorite to mix the chemicals for a first time period allowing the chemical to react to completion resulting in chlorine dioxide solution.

19. The laundry sanitizer of claim 15, further comprising the addition of 0 to 0.5% of an organic acid or its alkali metal salt to the solution containing chlorine dioxide where in the solution pH and the pka of the organic acid are within about 1 pH unit so that the organic acid functions as a pH buffer to maintain formula pH.

* * * * *